(12) United States Patent
Inoue

(10) Patent No.: US 6,537,284 B1
(45) Date of Patent: Mar. 25, 2003

(54) DEVICE FOR GUIDING AN APPLIANCE

(76) Inventor: Kanji Inoue, 98-13, Miyazaki-cho, Shimogamo, Sakyo-ku, Kyoto-shi, Kyoto 606-0802 (JP)

( * ) Notice: Subject to any disclaimer, the term of this patent is extended or adjusted under 35 U.S.C. 154(b) by 0 days.

(21) Appl. No.: 09/581,963

(22) PCT Filed: Oct. 29, 1998

(86) PCT No.: PCT/JP98/04909

§ 371 (c)(1),
(2), (4) Date: Aug. 15, 2000

(87) PCT Pub. No.: WO00/25847

PCT Pub. Date: May 11, 2000

(51) Int. Cl.$^7$ ................................................. A61F 2/00
(52) U.S. Cl. ...................... 606/108; 623/1.11; 623/1.23
(58) Field of Search ............................... 623/1.11, 1.23; 606/108, 195, 198; 604/284

(56) References Cited

U.S. PATENT DOCUMENTS

| 3,304,557 A | 2/1967 | Polansky |
| 4,300,244 A | 11/1981 | Bokros |
| 4,313,231 A | 2/1982 | Koyamada |
| 4,338,934 A | 7/1982 | Spademan |
| 4,872,874 A | 10/1989 | Taheri |
| 5,098,406 A | 3/1992 | Sawyer |
| 5,104,399 A | 4/1992 | Lazarus |
| 5,151,105 A | 9/1992 | Kwan-Gett |
| 5,183,085 A | 2/1993 | Timmermans |
| 5,199,948 A | 4/1993 | McPhee |

(List continued on next page.)

FOREIGN PATENT DOCUMENTS

| DE | 4219949 | 12/1993 |
| EP | 0 464 755 A1 | 1/1992 |
| EP | 0472731 | 3/1992 |
| EP | 0786267 A1 | 7/1997 |
| EP | 0858784 A2 | 8/1998 |
| EP | 0933070 A2 | 8/1999 |
| GB | 2164562 | 3/1986 |
| JP | 3-236836 | 10/1991 |
| JP | 4-25755 | 2/1992 |
| JP | 4-263852 | 9/1992 |

(List continued on next page.)

OTHER PUBLICATIONS

Kanji Inuoe, et al., Aortic Arch Reconstruction by Transluminally Placed Endovascular Branched Stent Graft, Nov. 9, 1999, pp. II–316–321, vol. 100, No. 19, *Circulation* Supplement, Lippincott Williams & Wilkins.

*Primary Examiner*—Kevin Shaver
*Assistant Examiner*—Michael B. Priddy
(74) *Attorney, Agent, or Firm*—Banner & Witcoff, Ltd.

(57) ABSTRACT

A device for guiding a branched artificial blood vessel 1 having a tubular main body 5 with collapsible/restorable elasticity and a branch portion 6 with collapsible/restorable elasticity which branches from a part of the main body 5 with its internal space communicating with the main body 5, which artificial blood vessel 1 has been transferred as collapsed in a main blood vessel 2 to a branched part 4 branching a branch blood vessel 3 from the main blood vessel 2, the device being utilized in inserting the branch portion 6 of the artificial blood vessel 1 into the branch blood vessel 3, the device comprising an operating rod 9a inserted into the main body 5 from a trailing open end thereof and operable for rotation by hand, a guiding rod 9b continuously connected to the operating rod 9a so as to be capable of turning around with rotation of the operating rod 9a and having a leading end extending to an open end of the branch portion, and mooring means 9c for releasably mooring the branch portion by a portion adjacent the open end thereof to the guiding rod 9b, wherein when the main body is moved backward with the guiding rod 9b made to assume a predetermined position by turning, the branch portion 6 accompanying the guiding rod 9b is capable of advancing into the branch blood vessel 3 together with the guiding rod 9b.

28 Claims, 9 Drawing Sheets

U.S. PATENT DOCUMENTS

| | | |
|---|---|---|
| 5,207,695 A | 5/1993 | Trout, III |
| 5,234,456 A | 8/1993 | Silvestrini |
| 5,236,447 A | 8/1993 | Kubo et al. |
| 5,242,452 A | 9/1993 | Inuoe |
| 5,290,305 A | 3/1994 | Inoue |
| 5,330,528 A | 7/1994 | Lazim |
| 5,383,926 A | 1/1995 | Lock et al. |
| 5,387,235 A | 2/1995 | Chuter |
| 5,405,331 A | 4/1995 | Behnke et al. |
| 5,507,767 A | 4/1996 | Maeda et al. |
| 5,507,771 A | 4/1996 | Gianturco |
| 5,520,641 A | 5/1996 | Behnke et al. |
| 5,538,505 A | 7/1996 | Weinstein et al. |
| 5,554,181 A | 9/1996 | Das |
| 5,562,724 A | 10/1996 | Vorwerk et al. |
| 5,562,726 A * | 10/1996 | Chuter .......................... 623/1 |
| 5,569,205 A | 10/1996 | Hart et al. |
| 5,591,228 A * | 1/1997 | Edoga ....................... 623/1.11 |
| 5,607,445 A | 3/1997 | Summers |
| 5,609,627 A * | 3/1997 | Goicoechea et al. ....... 623/1.11 |
| 5,609,628 A | 3/1997 | Keranen |
| 5,628,783 A | 5/1997 | Quiachon et al. |
| 5,665,117 A | 9/1997 | Rhodes |
| 5,676,671 A | 10/1997 | Inoue |
| 5,693,089 A | 12/1997 | Inoue |
| 5,755,772 A | 5/1998 | Evans et al. |
| 5,755,773 A | 5/1998 | Evans et al. |
| 5,755,777 A * | 5/1998 | Chuter ...................... 623/1.11 |
| 5,782,904 A | 7/1998 | White et al. |
| 5,824,037 A | 10/1998 | Fogarty et al. |
| 5,860,998 A * | 1/1999 | Robinson et al. ........... 606/194 |
| 5,925,076 A | 7/1999 | Inoue |
| 5,976,179 A | 11/1999 | Inoue |
| 6,013,100 A | 1/2000 | Inoue |
| 6,045,557 A * | 4/2000 | White et al. ................. 606/108 |
| 6,056,775 A * | 5/2000 | Borghi et al. ................ 623/1.6 |
| 6,183,504 B1 * | 2/2001 | Inoue ........................ 623/1.11 |
| 6,197,046 B1 * | 3/2001 | Piplani et al. ............. 623/1.11 |
| 6,245,097 B1 | 6/2001 | Inoue |
| 6,254,593 B1 * | 7/2001 | Wilson ..................... 623/1.11 |
| 6,254,629 B1 | 7/2001 | Inoue |
| 6,254,630 B1 | 7/2001 | Inoue |
| 6,261,316 B1 * | 7/2001 | Shaolian et al. ........... 623/1.11 |
| 6,261,317 B1 | 7/2001 | Inoue |
| 6,270,520 B1 | 8/2001 | Inoue |
| 6,342,046 B1 | 1/2002 | Inoue |
| 6,346,118 B1 * | 2/2002 | Baker et al. ............... 623/1.12 |
| 2001/0020184 A1 * | 9/2001 | Dehdashtian et al. ...... 623/1.16 |

FOREIGN PATENT DOCUMENTS

| | | |
|---|---|---|
| JP | 5-212121 | 8/1993 |
| JP | 7-24072 | 1/1995 |
| JP | 3009638 | 2/1995 |
| JP | 6-63155 | 3/1995 |
| JP | 9-506524 | 6/1997 |
| JP | 9-511160 | 11/1997 |
| JP | 10-506292 | 6/1998 |
| WO | 91/12047 | 8/1991 |
| WO | 95/05788 | 2/1995 |
| WO | 95/16406 | 6/1995 |
| WO | 95/21592 | 8/1995 |
| WO | 95/34255 | 12/1995 |
| WO | 96/36297 | 11/1996 |
| WO | 96/36387 | 11/1996 |

* cited by examiner

DEVICE FOR GUIDING AN APPLIANCE

TECHNICAL FIELD

The present invention relates to a device for advantageously guiding appliances to be implanted which belong to the field of medical devices, particularly for guiding artificial blood vessels.

BACKGROUND ART

With the recent progress of medical technique, the art enabling transvascular use of a variety of appliances such as artificial blood vessels without ventrotomy has reached the clinical stage. Specific examples of such art include a method of transferring and fixing an artificial blood vessel using a catheter which has been invented by the inventor of the instant invention and disclosed in literature A (for example, PCT/JP96/01347 which has been published with International Publication No. WO96/36387). This method includes: inserting a catheter into a human body through an inguinal artery to position the leading end thereof near an affected part in which an aneurysm or a like pathological change is present; inserting in a collapsed condition a tubular artificial blood vessel imparted with collapsible/restorable elasticity into the catheter; transferring the artificial blood vessel to a predetermined location near the affected part by the use of a transferring device or a hauling device; and releasing the artificial blood vessel from the catheter, thereby positioning the artificial blood vessel in the affected vascular part having the aneurysm.

An artery has a branched part at which a branch blood vessel extends from the main vessel. Where an aneurysm is present in such a branched part, it is impossible to apply the above method simply. In an attempt to enable a transvascular treatment for an aneurysm in such a case, the inventor of the instant invention has also proposed in the above literature a method including: forming a branched artificial blood vessel comprising a main body and a branch portion; transferring the artificial blood vessel in the main blood vessel to a branched part thereof; and drawing the branch portion of the artificial blood vessel into a branch blood vessel branching from the main blood vessel, thereby positioning the artificial blood vessel conformally to the branched configuration of the subject blood vessel.

In the latter method, the artificial blood vessel is accompanied by an auxiliary hauling device adapted to drag the branch portion of the artificial blood vessel independently when the artificial blood vessel is transferred in the main vessel to the branched part by a transferring device, and the hauling device is drawn into the branch blood vessel by catching it using a catcher inserted from the branch side and taken out of the body so as to be operated for drawing the branch portion of the artificial blood vessel into the branch blood vessel. However, if the subject main blood vessel is an artery that terminates in peripheral blood vessels such as the celiac artery, it is difficult for any appliance to reach a desired part from a surface of the body. In such a case, it becomes impossible to insert the catcher from the outside of the body or take the hauling device out of the body, thus resulting in a disadvantage that the proposed method cannot be used.

DISCLOSURE OF INVENTION

To solve the foregoing problem, the present invention provides a device for guiding a branched appliance having a tubular main body with collapsible/restorable elasticity and a branch portion with collapsible/restorable elasticity which branches from a part of the main body with its internal space communicating with the main body, which appliance has been transferred as collapsed in a main blood vessel to a branched part branching a branch blood vessel from the main blood vessel, the device being utilized in inserting the branch portion of the appliance into the branch blood vessel, characterized by comprising an operating rod inserted into the main body from a trailing open end thereof and operable for rotation by hand, a guiding rod continuously connected to the operating rod so as to be capable of turning around with rotation of the operating rod and having a leading end extending to an open end of the branch portion, and mooring means for releasably mooring the branch portion by a portion adjacent the open end thereof to the guiding rod, wherein when the main body is moved backward with the guiding rod made to assume a predetermined position by turning, the branch portion accompanying the guiding rod is capable of advancing into the branch blood vessel together with the guiding rod.

Preferred embodiments of the present invention include such an arrangement that the operating rod and the guiding rod are formed by turning up a flexible wire rod into a loop having a trailing side forming the operating rod and a leading side forming the guiding rod.

For more reliable turning of the guiding rod by the force applied to the operating rod, it is desired that the leading side and the trailing side of the loop be in contact with each other and the contact portion be fixed.

For easy removal of the wire rod after the appliance has been guided, the fixing of the contact portion is releasably made using a snare wire.

A feature such that at least a portion of the loop protrudes beyond a leading open end of the main body is effective for preventing the wire rod from receiving an unexpected flexing force.

To enhance the guiding ability of the guiding rod, it is desired that the guiding rod comprise a tube and a guiding wire retractably accommodated in the tube with its leading end protruding from a leading end of the tube.

In another aspect, the present invention provides a device for guiding an appliance comprising an operating rod inserted into the main body from a trailing open end thereof and operable for rotation by hand, a guiding rod continuously connected to the operating rod so as to be capable of turning around with rotation of the operating rod and having a leading end extending to an open end of the branch portion, and mooring means for releasably mooring the branch portion by a portion adjacent the open end thereof to the guiding rod, wherein when the main body is moved forward with the guiding rod made to assume a predetermined position by turning, the branch portion accompanying the guiding rod is inserted into the branch blood vessel together with the guiding rod.

Specific embodiments of this case include an arrangement wherein the operating rod and the guiding rod are formed by bending a flexible wire rod into a curve having a trailing side forming the operating rod and a leading side forming the guiding rod.

In this case also, the guiding rod preferably comprises a tube having a guiding wire accommodating bore, and a guiding wire retractably accommodated in the guiding wire accommodating bore of the tube with its leading end protruding from a leading end of the tube.

For simultaneous releasing of the appliance from a moored state and from a collapsed state, it is desired that a mooring wire serving also as collapsing means for maintaining the branch portion of the appliance in the collapsed state be provided. By drawing out the mooring wire, restoration of the branch portion can be accomplished simultaneously with the releasing of the appliance from the moored state.

An advantageous embodiment of the mooring means comprises a mooring wire forming an openable closed circuit in cooperation with the tube, the mooring wire being capable of mooring the branch portion when the closed circuit is formed by inserting the mooring wire into a portion of the branch portion and capable of releasing the mooring state when the closed circuit is opened by drawing the mooring wire out of the branch portion, wherein at least a portion of the mooring wire that extends from a location adjacent the mooring portion toward a trailing side of the tube is positioned out of the guiding wire accommodating bore.

Specific examples of this arrangement include: one in which the tube has a portion provided with a window exposing the guiding wire accommodating bore and a mooring wire passing portion formed on an outer periphery of the tube at a location away from the window toward the trailing side of the tube, the mooring wire being passed through the mooring wire passing portion and drawn into the guiding wire accommodating bore through the window to form the closed circuit; one in which the tube is provided with two longitudinally-spaced mooring wire passing portions attached to the outer periphery thereof through which the mooring wire is passed to form the closed circuit in cooperation with the tube; and one in which the tube is provided with two longitudinally-spaced windows exposing the guiding wire accommodating bore, and the mooring wire is drawn into the guiding wire accommodating bore through that window situated on the trailing side of the tube and drawn out of that window situated on the leading side of the tube to form the closed circuit defined by the window on the leading side and the tube. Other specific examples of the arrangement include: one in which the tube is provided with three longitudinally-spaced windows exposing the guiding wire accommodating bore, and the mooring wire is drawn into the guiding wire accommodating bore through that window situated on the trailing side of the tube, then drawn out of the tube through the intermediate window, and again drawn into the guiding wire accommodating bore through that window situated on the leading side of the tube, to form the closed circuit defined by the drawn-out portion of the mooring wire and the tube; one in which the tube comprises a pair of tube elements integrally related to each other and having respective wire accommodating bores, one bore serving as a guiding wire accommodating bore accommodating the guiding wire, the other bore serving as a mooring wire accommodating bore accommodating the mooring wire, and the tube element having the mooring wire accommodating bore is provided with a window exposing the mooring wire accommodating bore to form the closed circuit defined by the window and the corresponding tube element; and one in which the tube defines therein two wire accommodating bores separated from each other with an intermediate partition wall, one serving as a guiding wire accommodating bore accommodating the guiding wire, the other serving as a mooring wire accommodating bore accommodating the mooring wire, and the tube is provided with a window exposing the mooring wire accommodating bore to w form the closed circuit defined by the window and the tube.

The mooring means as described above is widely applicable to devices for guiding a common appliance as well as a branched appliance. Such a guiding device comprises a guiding rod, and mooring means for releasably mooring an appliance to the guiding rod, the guiding rod comprising a tube and a guiding wire retractably accommodated in the tube with its leading end protruding from a leading end of the tube, the mooring means comprising a mooring wire forming an openable closed circuit in cooperation with the tube, the mooring wire being capable of mooring the appliance when the closed circuit is formed by inserting the mooring wire into a portion of the appliance and capable of releasing the mooring state when the closed circuit is opened by drawing the mooring wire out of the appliance, wherein at least a portion of the mooring wire that extends from a location adjacent the mooring portion toward a trailing side of the tube is positioned out of a guiding wire accommodating bore.

The closed circuit can be formed in a manner similar to those described for the aforementioned branched appliance.

With the guiding device of the present invention, the appliance is transferred to a branched portion of a blood vessel by a typical method, and then the guiding rod is caused to turn around by rotating the operating rod so that the leading end of the guiding rod is positioned near the entrance of the branch blood vessel. Then, the guiding rod is inserted into the branch blood vessel by moving the appliance backward, and as the guiding rod goes forward, the branch portion of the appliance which is moored to the guiding rod by the mooring means is guided into the branch blood vessel. For this reason, there is no need to take any operating member or the like in and out of the branch blood vessel from the terminating side thereof. Thus, the present invention can effectively be applied to the case where it is difficult for any appliance to reach a desired location from a body surface because of the subject blood vessel terminating in peripheral vessels in an internal organ like the celiac artery. Particularly where the appliance is an artificial blood vessel and the branch blood vessel branches downstream from the main blood vessel such as the celiac artery, the guiding device of the present invention can smoothly guide the branch portion of the artificial blood vessel into the branch blood vessel since the branch portion is moved toward the branch blood vessel when the branched appliance is moved backward from the branched part of the subject blood vessel.

If the flexible wire rod is configured into a loop, the leading end of the wire is directed backward, i.e., toward the downstream direction. This feature enables the leading end of the wire rod to be readily positioned as facing opposite to the opening of the branch blood vessel, while forming the operating rod and the guiding rod using a single member. Further, the guiding rod can turn around effectively by the rotative force applied to the operating rod.

In this case, if the contact portion of the loop is fixed, the rotative force applied to the operating rod is directly converted into a turning operation of the guiding rod through the fixed contact portion while transmission of the rotative force merely as a rotative force through the loop to the guiding rod is prevented. Such transmission would otherwise occur if the contact portion is not fixed. Thus, this feature enables more reliable transmission of rotational torque.

If the contact portion of the loop is fixed using the snare wire, the looping can be released easily after the guidance of the appliance has been accomplished, and the guiding device can be particularly effectively withdrawn from the branched part in a compactly collapsed fashion.

If at least a portion of the loop protrudes beyond the leading open end of the main body, it is possible to effectively reduce the danger of bending the loop undesirably as compared with the case where the loop is forcibly made within the narrow main body.

Where the guiding rod comprises a tube and a guiding wire, it is possible to insert first the guiding wire into the branch blood vessel and then the tube accompanied by the branch portion of the appliance thereinto under the guidance of the guiding wire. With this feature, it is possible to locate the entrance of the branch blood vessel by utilizing the flexibility of the guiding wire even when the guiding wire is fairly remote therefrom, thereby effectively enhancing the ability to guide the branch portion of the appliance into the branch blood vessel.

The guiding device of the present invention may be arranged such that the branch portion of the appliance is guided into the branch blood vessel by moving the appliance forward instead of moving it backward. This arrangement makes no difference from the arrangement designed to guide the appliance into the branch blood vessel by moving it backward in that there is no need to take any operating member in and out of the terminating side of the branch blood vessel. Thus, this arrangement also can effectively be applied to the case where it is difficult for an appliance to reach a desired location from a body surface because of the subject blood vessel terminating in peripheral blood vessels in an internal organ like the celiac artery.

When the guiding device comprises a wire rod, the operating rod and the guiding rod can be formed by merely curving the wire rod.

In this case also, by forming the guiding rod comprising a tube and a guiding wire, the ability to guide the branch portion to the branch blood vessel can be enhanced effectively.

If the mooring means has an additional function as collapsing means for collapsing the branch portion of the appliance, releasing the mooring means also causes the branch portion to be released from the collapsed state at the same time thereby allowing elastic restoration of the branch portion. Thus, the branch portion of the appliance once positioned at a desired location can achieve appropriate restoration through a series of operations.

If the mooring means mainly comprises a mooring wire forming a closed circuit in cooperation with the tube, this arrangement is simple and can reliably release the branch portion by only drawing the mooring wire from a remote location to open the closed circuit even when an intermediate portion is led around as curved in the subject blood vessel. Thus, a reliable transvascular treatment can be ensured. Further, since the trailing side of the mooring wire is positioned out of the guiding wire accommodating bore, the mooring wire is assuredly prevented from being inconveniently tangled with the guiding wire, while at the same time the mooring function and the guiding function can be rendered compatible with each other on the tube.

When the closed circuit is formed in each of the modes described above, the openable closed circuit of a simplified structure can assuredly realized using the mooring wire. Particularly where the tube is provided with a window and a mooring wire passing portion for insertion of the mooring wire, it is only required that the window be formed by punching a hole in a desired portion of the tube, and the mooring wire passing portion is formed by, for example, tying the tube with a string. Where the tube is provided with two mooring wire passing portions, it is only required that the two mooring wire passing portions be formed by tying desired portions of the tube with strings. Where the tube is provided with two or three windows, it is only required that holes be punched in desired portions of the tube. Alternatively, where the tube comprises two tube elements or the tube defines two wire accommodating bores, the mooring wire and the guiding wire can be assuredly parted from each other thereby preventing interference with each other.

It should be noted that the guiding device of the arrangement comprising a guiding rod, and mooring means for releasably mooring any type of appliance including an artificial blood vessel to the guiding rod, the guiding rod comprising a tube and a guiding wire retractably accommodated in the tube with its leading end protruding from a leading end of the tube, exhibits mooring and guiding abilities similar to those described above.

BEST MODE OF CARRYING OUT THE INVENTION

The present invention will now be described in detail by way of embodiments shown in the attached drawings.

First Embodiment

Figure 1:
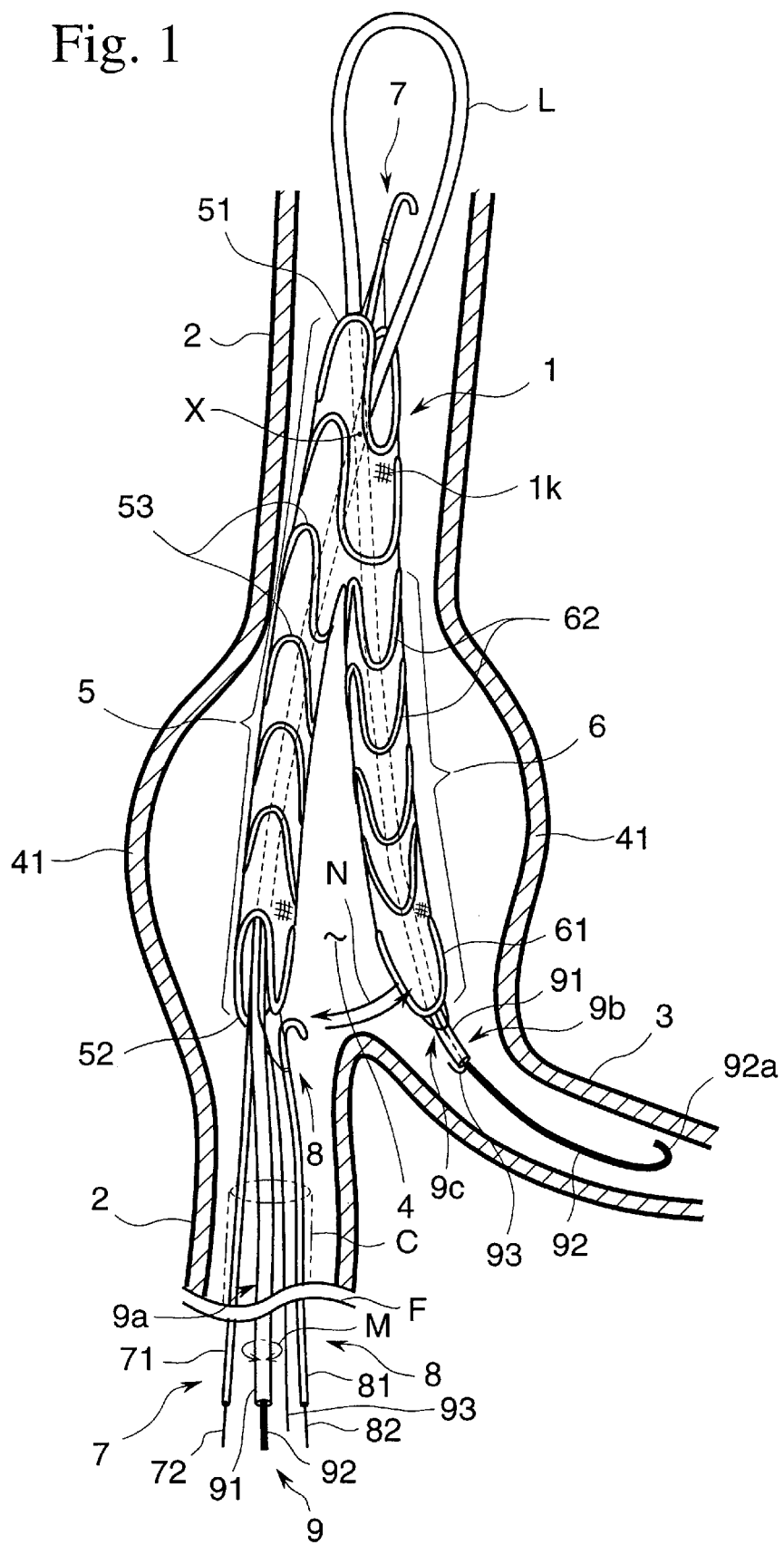
FIG. 1 is a sectional view illustrating a guiding device according to a first embodiment of the present invention in a state applied to a branched artificial blood vessel.

FIG. 1 illustrates a state where a branched artificial blood vessel 1 used as an appliance in this embodiment is transferred to a branched part 4 at which a branch blood vessel 3 branches from a main blood vessel 2 by being moved forward as collapsed in the main blood vessel 2. The main blood vessel 2 is, for example, the abdominal aorta, and the branch blood vessel 3 is, for example, the celiac artery. The branched artificial blood vessel 1 is designed to be implanted over an aneurysm 41 which is present in the branched part 4, thereby preventing blood from flowing around the aneurysm 41. The artificial blood vessel 1 is Y-shaped comprising a main body 5 to be positioned within the main blood vessel 2 and a branch portion 6 to be positioned within the branch blood vessel 3. Respective examples of the structure of artificial blood vessel 1 and the method of transferring an artificial blood vessel to a branched part of a blood vessel are described in detail in, for example, the foregoing literature A (PCT/JP96/01347 internationally published as WO96/36387) which has been disclosed by the inventor of the instant invention. The basic portion of this embodiment is summarized below according to the literature A. The main body 5 of the artificial blood vessel 1 has a skeleton comprising end ring members 51 and 52 having collapsible/restorable elasticity, and intermediate ring members 53 having collapsible/restorable elasticity interposed between the end ring members 51 and 52. The branch portion 6 of the artificial blood vessel 1 has a skeleton comprising an end ring member 61 in juxtaposed relationship with the end ring member 52, and intermediate ring members 62 interposed between the end ring member 61 and one of the intermediate ring members 53 of the main body 5. These ring members 51, 52, 53, 61 and 62 are integrally covered with a flexible, extensible and waterproof tubular cover 1k of Y configuration.

Figure 2:
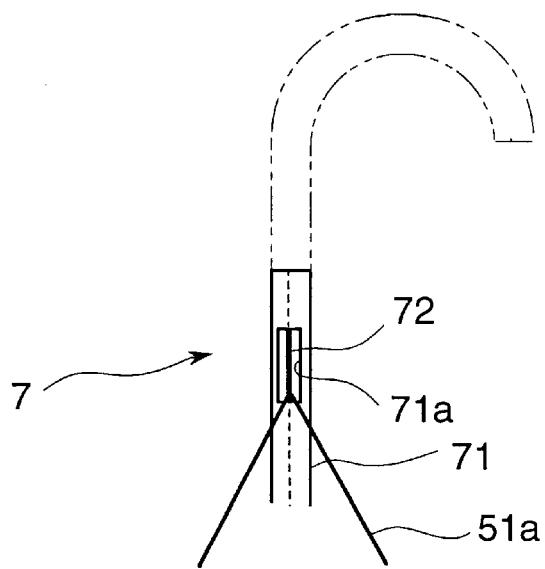
FIG. 2 is an enlarged fragmentary view showing a transferring device and a hauling device shown in FIG. 1.
Figure 2:
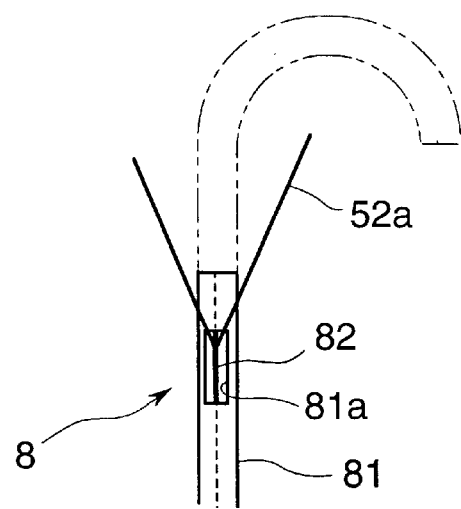

The artificial blood vessel 1 is provided with a transferring device 7 for driving the leading end ring member 51 of the main body 5 forward and a hauling device 8 for hauling the trailing end ring member 52 backward. As shown in FIGS. 1 and 2, the transferring device 7 comprises a tube 71 and a wire 72 accommodated in the tube 71. The wire 72 is drawn out of the tube 71 through a perforation 71a of the tube 71 for engagement with a catching string 51a attached to the leading end ring member 51 and then drawn into the tube 71 again, thereby making the transferring device 7 engage and hold the leading end ring member 51. Similarly, the hauling device 8 comprises a tube 81 and a wire 82 accommodated in the tube 81. The wire 82 is drawn out of the tube 81 through a perforation 81a of the tube 81 for engagement with a catching string 52a attached to the trailing end ring member 52 and then drawn into the tube 81 again, thereby making the hauling device 8 engage and hold the trailing end ring member 52.

More specifically, a catheter (C) is inserted into a human body from an inguinal artery at a groin (F) of the thigh using a sheath (not shown) until the leading end thereof is positioned near an affected part in which an aneurysm or the like is present. Subsequently, the artificial blood vessel 1 as collapsed using a string so as not to expand spontaneously is inserted into the catheter (C) and moved forward using the transferring device 7 to the branched part 4 affected by an aneurysm 41. Then, the catheter (C) is moved backward with the transferring device 7 kept in the same position to release the artificial blood vessel 1 in the branched part 4 at which the branch blood vessel 3 branches from the main blood vessel 2. Individual collapsing devices are separately used for the main body 5 and the branch portion 6. For example, the collapsing device for the main body 5 is such that the ring members 51 to 53 are each bent into a wave having alternate top and bottom oriented in the advancing direction and then tied with a string (not shown), which in turn is bound with a single wire, to keep the bent state thereof. When the wire is drawn out, the string is released from its strained state, so that the ring members 51–53 are released from their collapsed state. The same is true for the ring members 61 and 62 of the branch portion 6.

In this embodiment, the branch portion 6 is guided into the branch blood vessel 3 using a guiding device 9 of the present invention prior to releasing the binding of the string.

The guiding device 9 is operable for rotation by hand and comprises an operating rod 9a having a leading end to be inserted into the main body 5 from a trailing open end thereof, a guiding rod 9b continuously connected to the operating rod 9a so as to be capable of turning around and having a leading end extending to an open end of the branch portion 6, and mooring means 9c for releasably mooring the branch portion 6 by a portion adjacent the open end thereof to the guiding rod 9b. By moving the main body 5 backward when the guiding rod 9b has assumed a predetermined position by turning, the branch portion 6 accompanying the guiding rod 9b is inserted into the branch blood vessel 3 together with the guiding rod 9b.

The operating rod 9a and the guiding rod 9b are formed of a flexible wire rod (usually called "catheter"). This wire rod is turned up to form a loop (L), the trailing side of which forms the operating rod 9a, the leading side of which forms the guiding rod 9b. The leading side and trailing side of the loop (L) are brought into contact with each other, and the contact portion (X) is fixed by tying with a string or the like. The loop (L) is located so that the most part thereof protrudes from the open end of the main body 5 defined by the leading end ring member 51.

More specifically, the wire rod comprises a tube 91 and a guiding wire 92 retractably accommodated in the tube 91 with the leading end of the guiding wire 92 protruding from the leading end of the tube 91. In this embodiment, the guiding wire 92 has a leading end 92a shaped like a coil spring which is bent into a J shape.

Figure 7:
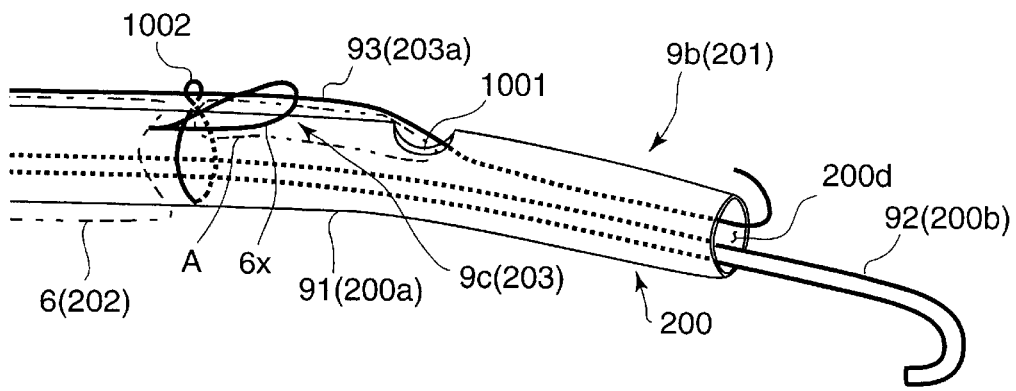
FIG. 7 is an explanatory view illustrating a specific arrangement of a guiding device according to a third embodiment of the present invention.

As illustrated in FIG. 7, the mooring means 9c comprises a mooring wire 93 forming an openable closed circuit (A) in cooperation with the tube 91. The mooring wire 93 is made to pass through a loop-shaped catching portion 6x formed on a portion of the branch portion 6 to form the closed circuit (A), thereby mooring the branch portion 6. When the closed circuit (A) is opened and then the mooring wire 93 is drawn out of the catching portion 6x, the moored state of the branch portion 6 is released. Detailed description thereof will be described later in THIRD EMBODIMENT. At least a portion of the mooring wire 93 that extends from a location adjacent the mooring portion toward the trailing side is drawn out of the tube 91 and laid on the outer periphery of the tube 91. The mooring wire 93 of the mooring means 9c serves also as a collapsing wire of the collapsing means for keeping the collapsed state of the branch portion 6. Thus, when the mooring wire 93 is drawn out, restoration of the branch portion 6 is achieved at the same time with the releasing of the branch portion 6 from its moored state.

Figure 3:
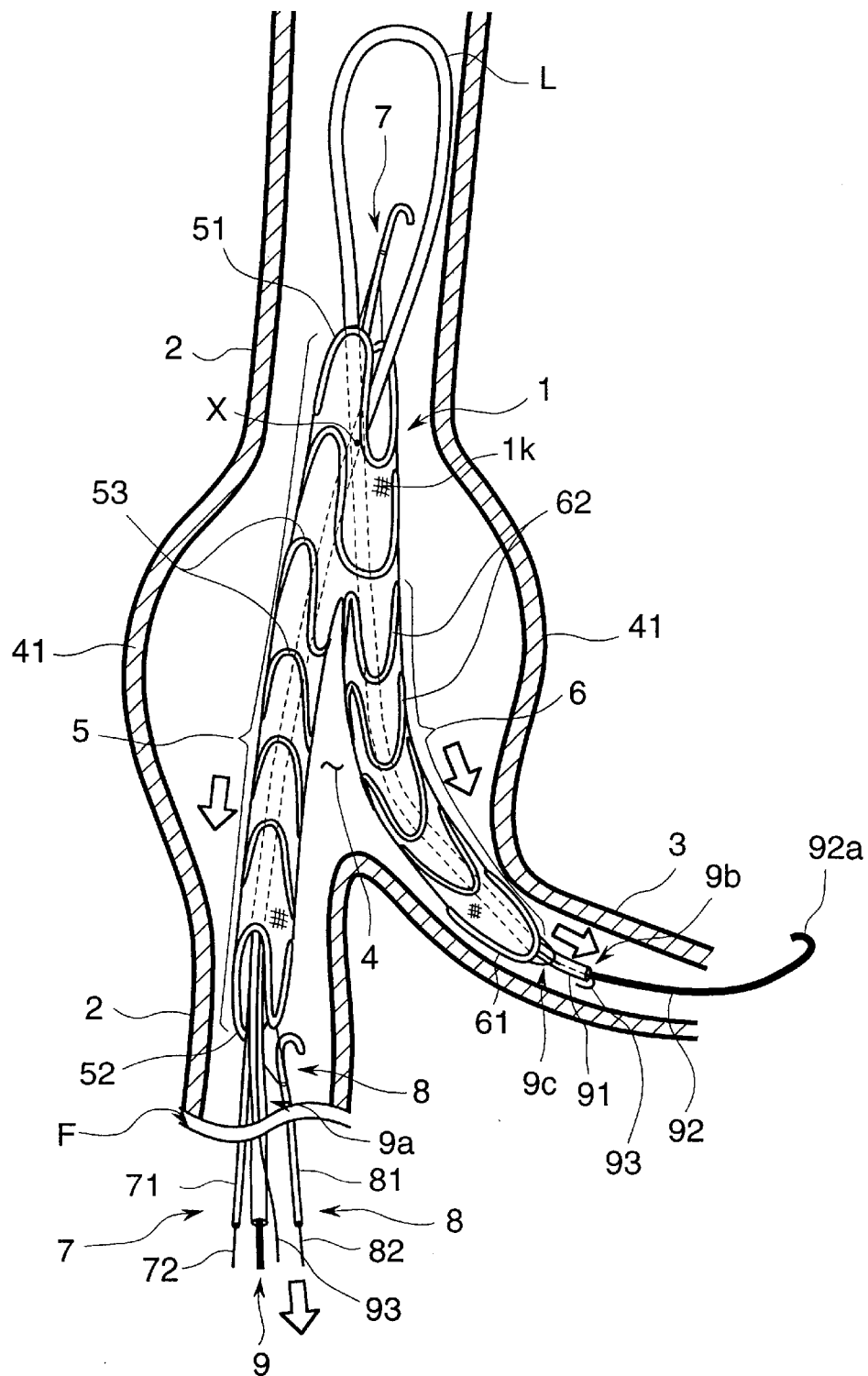
FIG. 3 is a sectional view, corresponding to FIG. 1, illustrating the handling procedure of the guiding device.
Figure 4:
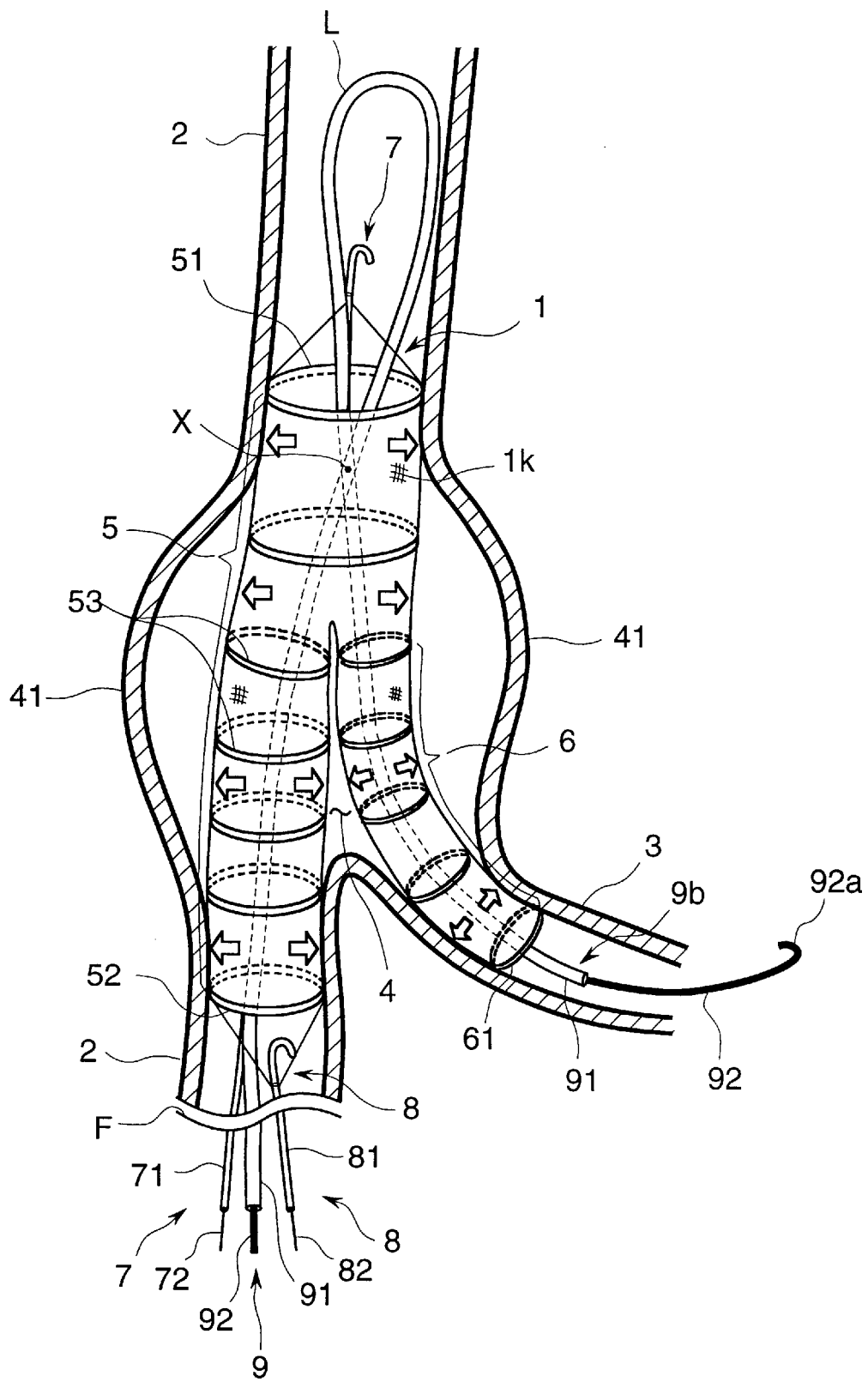
FIG. 4 is a sectional view, corresponding to FIGS. 1 and 2, illustrating the handling procedure of the guiding device.

In this embodiment, after the branched artificial blood vessel 1 released as collapsed from the catheter (C) is positioned slightly upstream of a desired fixing position adjacent the branched part 4 as shown in FIG. 1, the trailing side of the tube 91, or the operating rod 9a is operated for rotation as indicated by arrow (M) in FIG. 1 from the outside of the thigh (F) to cause the leading side of tube 91, or the guiding rod 9b to turn around as indicated by arrow (N) in FIG. 1 so that the leading end of the guiding rod 9b faces opposite to the entrance of the branch blood vessel 3. At this time, the guiding wire 92 has to assume a position retracted from the position shown. The positioning of the guiding rod 9b may be achieved while observing the guiding rod 9b by X-raying or the like. Once the positioning is done, the guiding wire 92 is pushed forward so that the leading end thereof is first inserted into the branch blood vessel 3. Thereafter, the hauling device 8 attached to the branched artificial blood vessel 1 is pulled to move the entire artificial blood vessel 1 backward. At this time, the guiding rod 9b forming the leading side of the tube 91 advances in the direction indicated by arrow in FIG. 3 to a predetermined position in the branch blood vessel 3 as accompanied by the branch portion 3 under the guidance of the guiding wire 92. When the branch portion 6 has reached a predetermined position and the branched artificial blood vessel 1 has wholly become in position, the collapsing device for the main body 5 is released to cause the main body 5 to elastically expand for restoration until it intimately contacts the internal wall of the main blood vessel 5. Subsequently, the branch portion 6 is released from the moored state by the mooring means 9c. At the same time therewith, the mooring means 9c releases the branch portion from the collapsed state also, with the result that the branch portion 6 expands elastically for restoration until it intimately contacts the internal wall of the branch blood vessel 3. Finally, the wires 72 and 82 of the transferring device 7 and hauling device 8 are drawn to undo the engagement with the ring members 51 and 52, and then the transferring device 7 and the hauling device 8 are withdrawn from the branched part 4, followed by withdrawal of the guiding device 9. One exemplary procedure for withdrawing the guiding device 9 includes the steps of: pressing forward the operating rod 9a temporarily to move the loop (L) up to a position at which the guiding rod 9b is upwardly drawn out of the main body 5 of the artificial blood vessel 1; moving forward the sheath (C) to a location adjacent the contact portion (X) of the loop (L); and drawing the operating rod 9a backward. This procedure causes the loop (L) and the guiding rod 9b to be drawn into the sheath (C) as collapsed. What is to be done thereafter for the withdrawal of the guiding device 9 is merely drawing the sheath (C) out of the human body. In this way, the artificial blood vessel 1 alone is left at the branched part 4, and thus, the transvascular implantation of the artificial blood vessel 1 is completed.

With the guiding device 9 described above, after the artificial blood vessel 1 has been transferred to the branched part 4 by the typical method, the leading end of the guiding rod 9b can be positioned as facing opposite to the entrance of the branch blood vessel 3 by operating the operating rod 9a for rotation to cause the guiding rod 9b to turn around. Subsequently, by moving the entire artificial blood vessel 1 backward from that position, the guiding rod 9b can be inserted into the branch blood vessel 3 for guiding the branch portion 6 accompanying the guiding rod 9b via the mooring means 9c into the branch blood vessel 3. For this reason, there is no need to take any operating member or the like in and out of the branch blood vessel 3 from the terminating side of the vessel. Thus, the present invention can effectively be applied to the case where it is difficult for an appliance to reach a desired location from a body surface because of the subject blood vessel terminating in peripheral vessels in an internal organ like the celiac artery. Particularly where the artificial blood vessel 1 is inserted into a human body gradually toward the center thereof against the flow of blood as in this embodiment, since the branch blood vessel 3 such as the celiac artery branches in the downstream direction from the main blood vessel 2 such as the abdominal aorta, the branching direction of the branch blood vessel 3 coincides with the moving direction of the branch portion 6 to be inserted into the branch blood vessel 3 by moving the artificial blood vessel 1 backward. Therefore, it is possible to smoothly guide the branch portion 6 into the branch blood vessel 3.

Particularly, since the guiding rod 9b is formed by looping the flexible wire rod, the leading end of the guiding rod 9b is oriented in the backward direction. Thus, the guiding rod 9a can readily be positioned as facing opposite to the opening of the branch blood vessel 3. Further, a single member can form both the operating rod 9a and the guiding rod 9b and, hence, a rotative force applied to the operating rod 9a effectively causes the guiding rod 9b to turn around.

In this case, since the contact portion (X) of the loop (L) is fixed, a rotative force applied to the operating rod 9a of the wire rod is directly converted into a turning operation of the guiding rod 9b via the contact portion (X) and hence is prevented from being transmitted as a mere rotative force (i.e., as mere rotation of the wire rod) to the guiding rod 9b. Such undesirable transmission can be expected when the contact portion (X) is not fixed. Thus, this feature enables more reliable transmission of rotative torque.

The loop (L) is formed such that at least a portion thereof protrudes from the leading open end of the main body 5. This makes it possible to assuredly avoid undesirable bending of a portion of the loop (L), unlike the case of the loop (L) formed within the narrow and small main body 5.

Further, since the guiding rod 9b as well as the operating rod 9a comprises the tube 91 and the guiding wire 92, it is possible that under the guidance of the guiding wire 92 precedently inserted into the branch blood vessel 3, the tube 91 accompanied by the branch portion 6 is introduced into the branch blood vessel 3. In addition, it is possible to locate the branch blood vessel 3 from a somewhat remote position by utilizing the flexibility of the guiding wire 92. Thus, the guiding device of the present invention can enjoy the guiding ability that is effectively enhanced.

Furthermore, since the mooring means 9c has a function of collapsing the branch portion 6 as well as the function of mooring the branch portion 6, releasing the mooring means 9c causes the branch portion 3 to be released from its collapsed state for elastic restoration at the same time. For this reason, the branch portion 6 at a predetermined location can restore its appropriate state through a series of operations.

In this embodiment, in withdrawing the wire rod the loop (L) together with the guiding rod 9b needs to be accommodated into the catheter (C) as superposed on the operating rod 9a in a bundle due to the loop (L) fixed by tying with a string or the like. This cannot deny that there arises some resistance to the withdrawing operation. Instead of this arrangement, use can be made of a so-called snare wire which is capable of expanding and contracting the loop by making the looped wire protrude and retract from the leading end of the tube. Such a snare wire enables easy release of the loop (L) from the fixed state after the guidance of the artificial blood vessel 1 is completed, and allows the looped wire to be collapsed compact for the withdrawal from the branched part 4.

Figure 13:
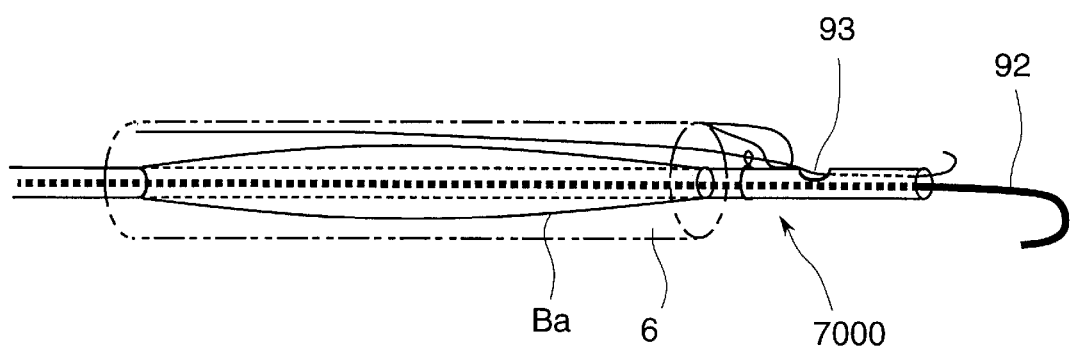
FIG. 13 illustrates a variation of the guiding device in which a balloon catheter is used instead of the wire rod shown in FIG. 1.

If the guiding device 9 is applied to each branch portion 6 of an artificial blood vessel having a plurality of branches from main body 5, such an artificial blood vessel can be guided and implanted to a branched part at which a plurality of branch blood vessels 3 extend from main blood vessel 2. Further, use of a balloon catheter 7000 as shown in FIG. 13 instead of the wire rod is effective. This balloon catheter 7000 defines therein two longitudinally extending bores, one for receiving air for expanding the balloon, the other for guiding wire 92 to be inserted therethrough. With this arrangement, the branch portion 6 of the artificial blood vessel 1 is moored by drawing the mooring wire 93 into the leading side of a balloon (Ba), and then the branch portion 3 is drawn into a predetermined position in the branch blood vessel 3 using the guiding wire 92, followed by releasing of the branch portion 3 from the moored state. Immediately after the releasing, the balloon (Ba) is expanded to press the branch portion 6 against the internal wall of the branch blood vessel 3. This arrangement does not require a separate introduction of a balloon catheter which would otherwise be done as required with the foregoing embodiment.

Second Embodiment

Figure 5:
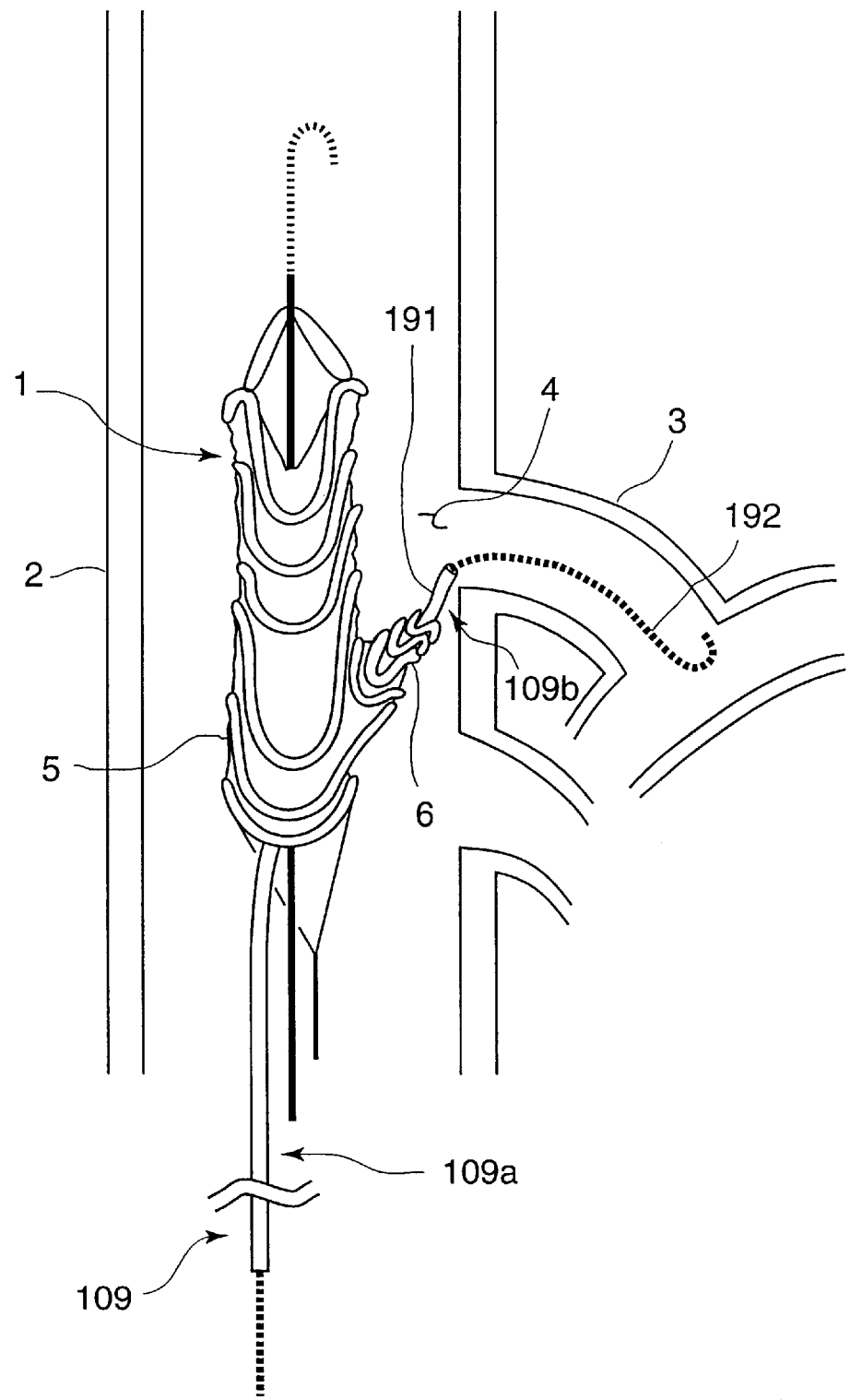
FIG. 5 is a sectional view illustrating a second embodiment of the present invention, corresponding to FIG. 1.
Figure 6:
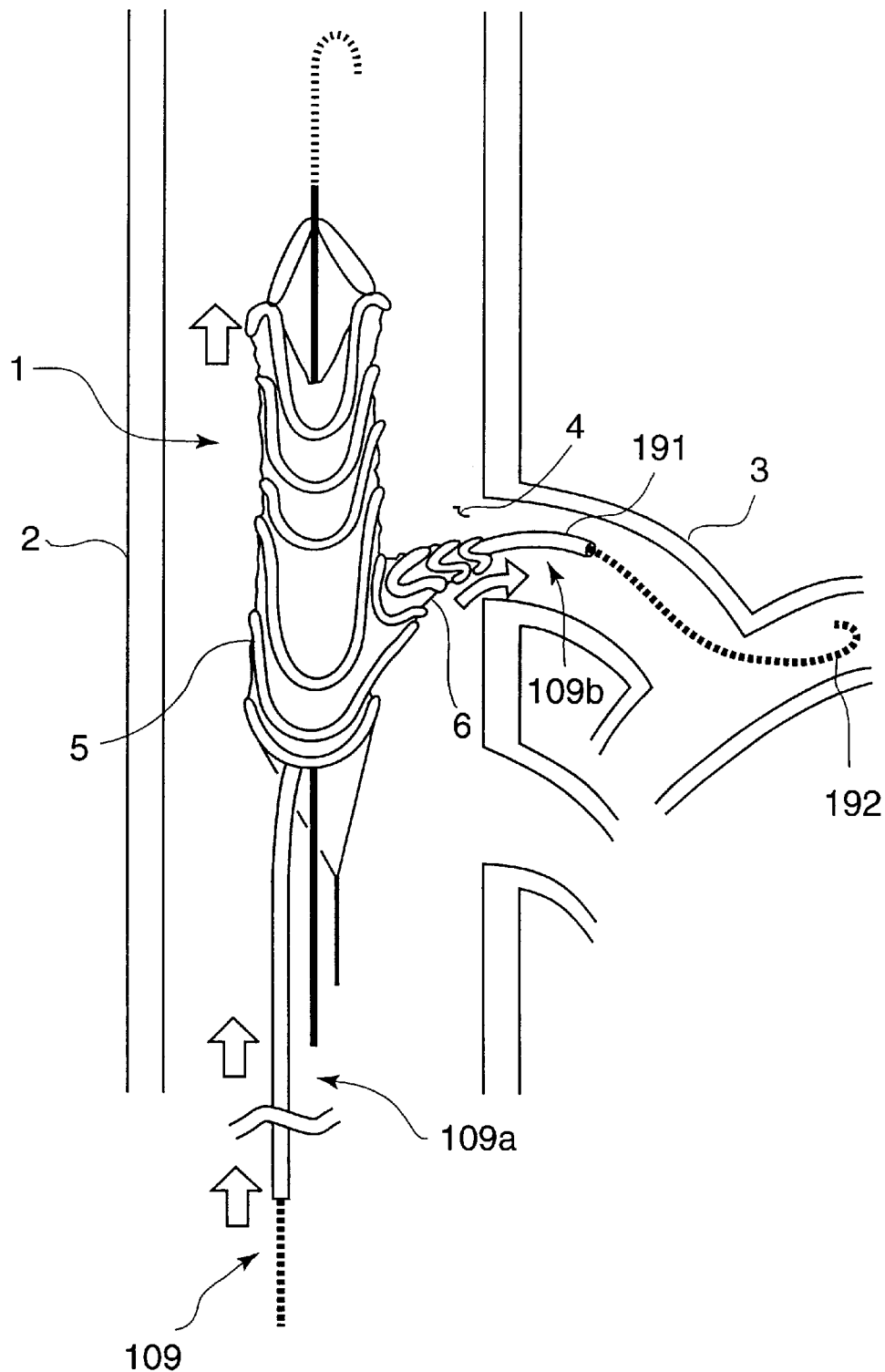
FIG. 6 is a sectional view, corresponding to FIG. 5, illustrating the handling procedure of the guiding device.

FIGS. 5 and 6 illustrate an arrangement to be used in introducing into the branch blood vessel 3 the branch portion 6 of artificial blood vessel 1 that has been transferred as collapsed in the main blood vessel 2 to a branched part 4 at which the branch blood vessel 3 branches from the main blood vessel 2, like the foregoing embodiment.

Guiding device 109 comprises an operating rod 109a inserted into the main body 5 from a trailing open end thereof and operable for rotation by hand, a guiding rod 109b continuously connected to the operating rod 9a so as to be capable of turning around with rotation of the operating rod 109a and having a leading end extending to an open end of the branch portion 6, the guiding rod 109b capable of entering the branch blood vessel 6 by moving the main body 5 forward when the guiding rod 9b has assumed a predetermined position by turning, and mooring means (not shown) for releasably mooring the branch portion 6 by a portion adjacent the open end thereof to the guiding rod 9b, as in the foregoing embodiment.

This guiding device 109 is adapted to insert the branch portion 6 into the branch blood vessel 3 not by moving the artificial blood vessel 1 backward but by moving it forward. This embodiment is different from the foregoing embodiment in that point. However, like the foregoing embodiment, there is no need to take any operating member or the like in and out of the branch blood vessel 3 from the terminating side of the branch blood vessel. Thus, this embodiment is also effectively applicable to the case where it is difficult for an appliance to reach a desired location from a body surface because of the subject blood vessel terminating in peripheral vessels in an internal organ like the celiac artery.

This embodiment also may employ a wire rod like a catheter to form the operating rod 109a and the guiding rod 109b easily. Besides, such a wire rod allows the leading end of the guiding rod 109b to orient obliquely forward easily and, hence, the guiding rod 109b can advantageously be inserted into the branch blood vessel 3 by utilizing the forward movement of the artificial blood vessel 1.

In this case also, by forming the guiding rod 109b comprising a tube 191 and a guiding wire 192 it is possible to effectively enhance the ability to guide the branch portion 6 into the branch blood vessel 3.

Third Embodiment

FIGS. 7 to 12 illustrate a plurality of guiding device 200 which are useful in guiding a variety of appliances including the foregoing artificial blood vessel 1.

The basic arrangement of guiding device 200 shown in FIG. 7 is applied to the foregoing first embodiment and summarized therein. The basic arrangement common to the devices shown in FIG. 7 and other drawings comprises a guiding rod 201, and mooring means 203 for releasably mooring any type of appliance 200, including artificial blood vessel 1, to the guiding rod 201, the guiding rod 201 comprising a tube 200a and a guiding wire 200b retractably accommodated in the tube 200a with its leading end protruding from a leading end of the tube 200a, the mooring means 203 comprising a mooring wire 203a forming an openable closed circuit (A) in cooperation with the tube 200a, the mooring wire 203a being capable of mooring the appliance 200 when the closed circuit (A) is formed by inserting the mooring wire 203a into a portion of the appliance 200 and capable of releasing the mooring state when the closed circuit (A) is opened by drawing the mooring wire 203a out of the appliance 200. Further, at least a portion of the mooring wire 203 that extends from a location adjacent the mooring portion toward a trailing side of the tube 200a is positioned out of a guiding wire accommodating bore 200d of the tube 200a. This arrangement can effectively prevent the mooring wire 203a and the guiding wire 200b from interfering with each other. Further, the function of accurately guiding the appliance 202 such as an artificial blood vessel by the guiding rod 201 using the guiding wire 200b is compatible with the function of reliably mooring and releasing the appliance 200 by the mooring wire 203a.

Description will be made of respective specific features, which slightly differ from each other, of the guiding devices 200 shown in respective drawings.

In the guiding device 200 shown in FIG. 7, a tube 200a has a portion provided with a window 1001 exposing a guiding wire accommodating bore 200d and a mooring wire passing portion 1002 attached to the tube 200a at a location away from the window 1001 toward a trailing side of the tube 200a, and the mooring wire 203a is passed through the mooring wire passing portion 1002 and drawn into the guiding wire accommodating bore 200d through the window 1001 to form the closed circuit (A). This arrangement can be formed by simply punching the tube 200a to form the window 1001 and winding a string around the tube 200a to form the mooring wire passing portion 1002.

Figure 8:
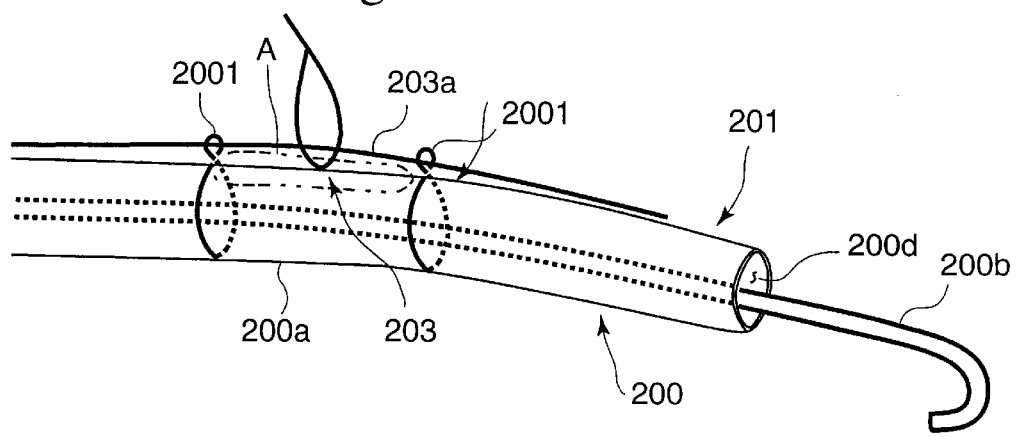
FIG. 8 illustrates a variation of the arrangement shown in FIG. 7.

In the guiding device 200 shown in FIG. 8, a tube 200a is attached with two longitudinally-spaced mooring wire passing portions 2001 through which a mooring wire 203 is passed to form the closed circuit (A) in cooperation with the tube 200a. This arrangement can be made by simply winding a string around the tube 200a at two points to form the mooring wire passing portions 2001. In this case, since the leading end of the mooring wire 203a is a free end, it is effective to bind the leading end with a string or the like as required.

Figure 9:
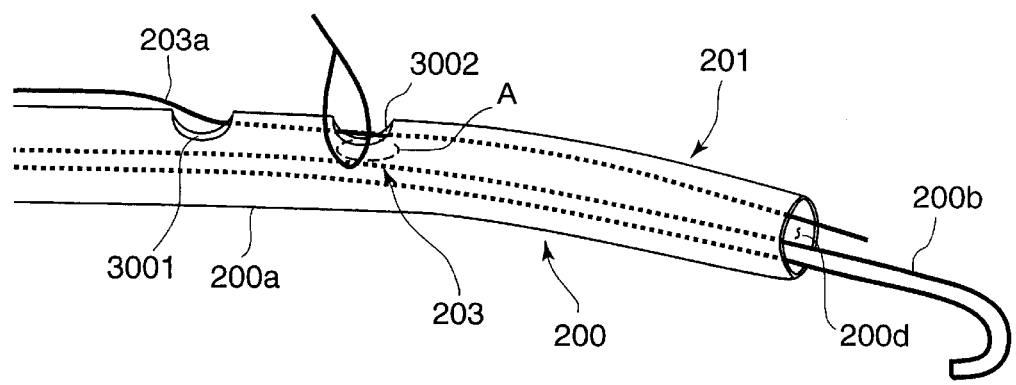
FIG. 9 illustrates another variation of the arrangement shown in FIG. 7.

In the guiding device 200 shown in FIG. 9, a tube 200a is provided with two longitudinally-spaced windows 3001 and 3002 exposing a guiding wire accommodating bore 200d, and a mooring wire 203 is drawn into the guiding wire accommodating bore 200d through window 3001 situated on a trailing side of the tube 200a and exposed through window 3002 situated on a leading side of the tube 200a to form the closed circuit (A) defined by the window 3002 and the tube 200a. This arrangement can be made by simply punching the tube 200a at two points to form the two windows 3001 and 3002.

Figure 10:
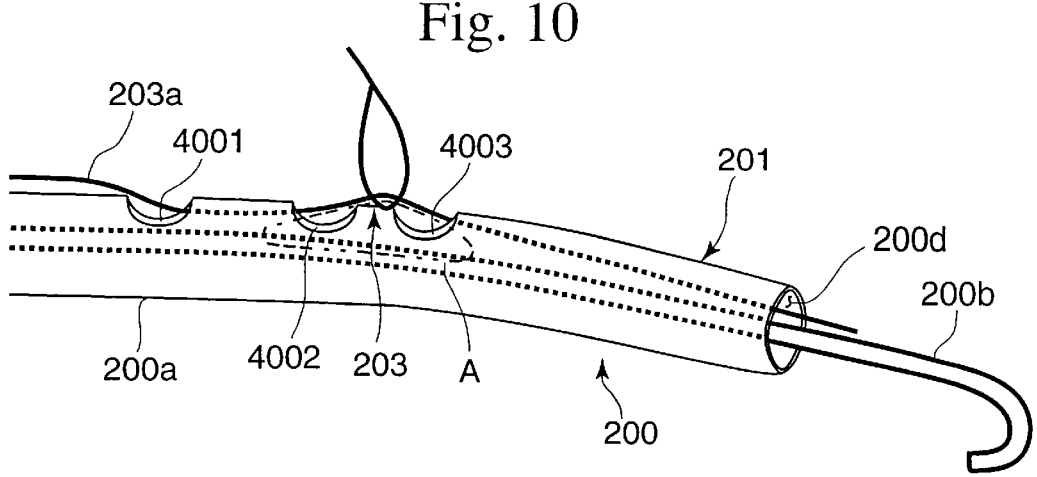
FIG. 10 illustrates yet another variation of the arrangement shown in FIG. 7.

In the guiding device 200 shown in FIG. 10, a tube 200a is provided with three longitudinally-spaced windows 4001, 4002 and 4003 exposing a guiding wire accommodating bore 200d, and a mooring wire 203a is drawn into the guiding wire accommodating bore 200d through the window 4001 situated on a trailing side of the tube 200a, then drawn out of the tube 200a through the intermediate window 4002, and again drawn into the guiding wire accommodating bore 200d through the window 4003, to form the closed circuit (A) defined by the drawn-out portion of the mooring wire 203a and the tube 200a. This arrangement can also be made by simply punching the tube 200a at three points to form the three windows 4001, 4002 and 4003.

Figure 11:
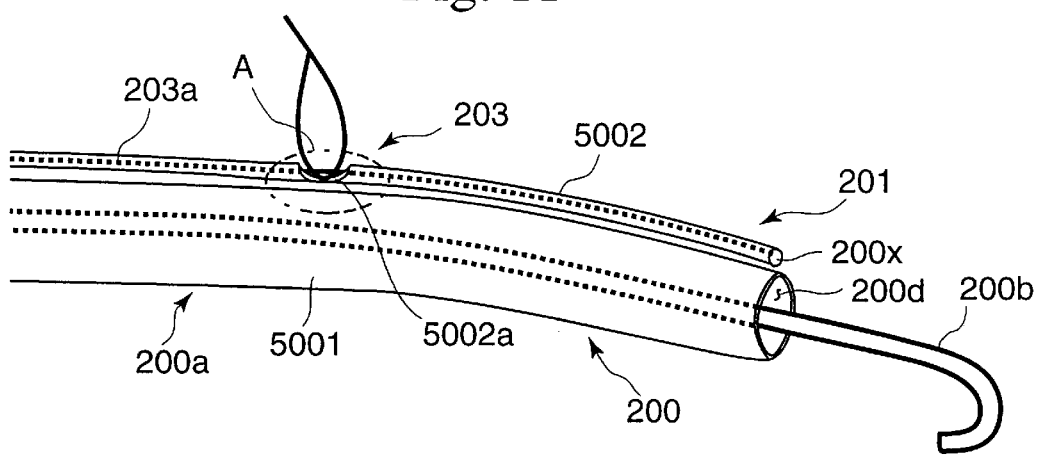
FIG. 11 illustrates y et another variation of the arrangement shown in FIG. 7.

In the guiding device 200 shown in FIG. 11, a tube 200a comprises a pair of tube elements 5001 and 5002 integrally related to each other and having respective wire accommodating bores 200d and 200x. The wire accommodating bore 200d of one tube element 5001 serves to accommodate a guiding wire 200b, while the wire accommodating bore 200x of the other tube element 5002 serves to accommodate a mooring wire 203a. The tube element 5002 is provided with a window 5002a exposing the mooring wire accommodating bore 200x to form the closed circuit (A) defined by the window 5002a and the tube element 5002. With this arrangement, the mooring wire 203a and the guiding wire 200b can be assuredly parted from each other and, hence, it is possible to prevent these wires from intertwining or entanglement due to mutual interference thereof.

Figure 12:
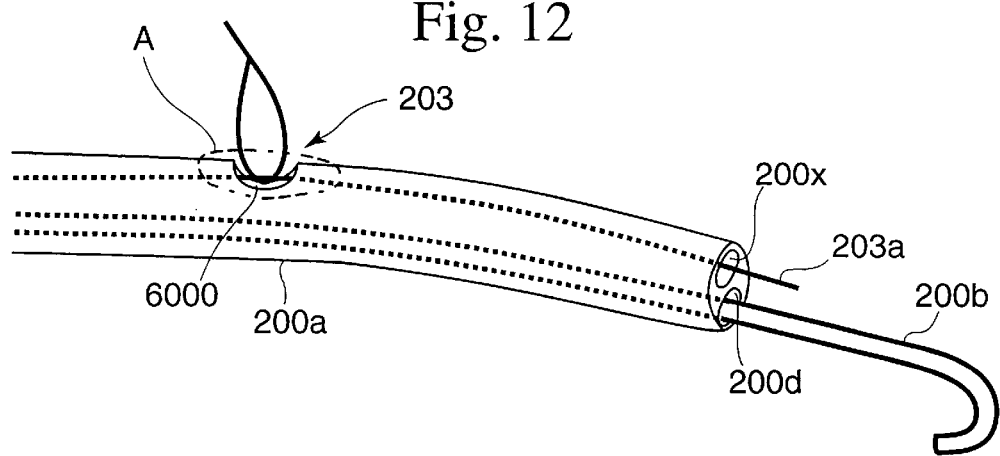
FIG. 12 illustrates a further variation of the arrangement shown in FIG. 7.

In the guiding device 200 shown in FIG. 12, a tube 200a defines therein two wire accommodating bores 200d and 200x separated from each other with an intermediate partition wall, one wire accommodating bore 200d serving to accommodate a guiding wire 200b, the other wire accommodating bore 200x serving to accommodate a mooring wire 203a. The tube 200a is provided with a window 6000 exposing the mooring wire accommodating bore 200x to form the closed circuit (A) defined by the window 6000 and the tube 200a. This arrangement also can assuredly separate the mooring wire 203a and the guiding wire 200b thereby preventing them from intertwining or entangling due to mutual interference.

While certain embodiments of the present invention have been described above, the specific arrangement or feature of each part of the embodiments is not limited to the foregoing embodiments and can be varied or modified in different ways without departing from the spirit of the present invention. In particular, the guiding devices of the first and second embodiments are applicable to branched appliances of diversified forms, and the guiding device of the third embodiment can be used to moor and guide a variety of appliances not limited to branched appliances.

Industrial Applicability

As has been described, the guiding device according to the present invention is highly useful in transvascularly implanting a branched artificial blood vessel to a branched part of a main blood vessel branching a peripheral blood vessel into which any type of appliance is difficult to insert. Further, the guiding device of the present invention can be used in various cases where an appliance needs to be moored and guided to a predetermined location.

What is claimed is:

1. A device for guiding a branched appliance having a tubular main body with collapsible/restorable elasticity and a branch portion with collapsible/restorable elasticity which branches from a part of the main body with its internal space communicating with the main body, which appliance has been transferred in a collapsed state in a main blood vessel to a branched part branching a branch blood vessel from the main blood vessel, the device being utilized in inserting the branch portion of the appliance into the branch blood vessel, said device comprising:

an operating rod insertable into the main body from a trailing open end thereof and operable for rotation by hand, a guiding rod continuously connected to the operating rod so as to be capable of turning around with rotation of the operating rod and having a leading end extendable to an open end of the branch portion, and mooring means for releasably mooring the branch portion by a portion adjacent the open end thereof to the guiding rod, wherein the device is usable such that when the main body is moved backward with the guiding rod made to assume a predetermined position by turning, the branch portion accompanying the guiding rod is capable of advancing into the branch blood vessel together with the guiding rod, and wherein the operating rod and the guiding rod are formed by turning up a flexible wire rod into a loop having a trailing side forming the operating rod and a leading side forming the guiding rod.

2. The device as set forth in claim 1, wherein the leading side and the trailing side of the loop are in contact with each other and the contact portion is fixed.

3. The device as set forth in claim 2, wherein the fixing of the contact portion is releasably made with a snare wire.

4. The device as set forth in claim 1, wherein at least a portion of the loop protrudes beyond a leading open end of the main body.

5. The device as set forth in claim 1, wherein: the guiding rod comprises a tube and a guiding wire retractably accommodated in the tube with its leading end protruding from a leading end of the tube; and the appliance is moored to the tube.

6. The device as set fourth in claim 5, wherein:

the mooring means comprises a mooring wire forming an openable closed circuit in cooperation with the tube, the mooring wire being capable of mooring the branch portion when the closed circuit is formed by inserting the mooring wire into a portion of the branch portion and being capable of releasing from a mooring state when the closed circuit is opened by drawing the mooring wire out of the branch portion; and at least a portion of the mooring wire extending from a location of the tube adjacent a mooring position and toward a trailing side of the tube is positioned outside of the guiding wire accommodating bore.

7. The device as set forth in claim 6, wherein the tube has a portion provided with a window exposing the guiding wire accommodating bore and a mooring wire passing portion formed on an outer periphery of the tube at a location away from the window toward the trailing side of the tube, the mooring wire being passed through the mooring wire passing portion and drawn into the guiding wire accommodating bore through the window to form the closed circuit in cooperation with the tube.

8. The device as set forth in claim 6, wherein the tube is provided with two longitudinally-spaced mooring wire passing portions attached to the outer periphery thereof through which the mooring wire is passed to form the closed circuit in cooperation with the tube.

9. The device as set fourth in claim 6, wherein the tube is provided with two longitudinally-spaced windows exposing the guiding wire accommodating bore, the mooring wire being drawn into the guiding wire accommodating bore through a first of said windows situated toward a trailing side of the tube and exposed through a second of said windows situated toward a leading side of the tube to form the closed circuit defined by the window situated toward the leading side and the tube.

10. The device as set fourth in claim 6, wherein the tube is provided with three longitudinally-spaced windows exposing the guiding wire accommodating bore, the mooring wire being drawn into the guiding wire accommodating bore through a first of said windows situated toward a trailing side of the tube, then drawn out of the tube through a second intermediate one of said windows, and again drawn into the guiding wire accommodating bore through a third one of said windows situated toward a leading side of the tube, to form the closed circuit defined by the drawn-out portion of the mooring wire and the tube.

11. The device as set forth in claim 6, wherein: the tube comprises a pair of tube elements integrally related to each other and having respective wire accommodating bores, one bore serving as a guiding wire accommodating bore accommodating the guiding wire, the other bore serving as a mooring wire accommodating bore accommodating the mooring wire; and the tube element having the mooring wire accommodating bore is provided with a window exposing the mooring wire accommodating bore to form the closed circuit defined by the window and the corresponding tube element.

12. The device as set forth in claim 6, wherein the tube defines therein two wire accommodating bores separated from each other with an intermediate partition wall, one serving as a guiding wire accommodating bore accommodating the guiding wire, the other serving as a mooring wire accommodating bore accommodating the mooring wire, and is provided with a window exposing the mooring wire accommodating bore to form the closed circuit defined by the window and the tube.

13. The device as set forth in claim 1, wherein the mooring means serves also as collapsing means for maintaining the branch portion of the appliance in the collapsed state, the mooring means being capable of allowing restoration of the branch portion and releasing the branch portion from its moored state simultaneously.

14. A device for guiding a branched appliance having a tubular main body with collapsible/restorable elasticity and a branch portion with collapsible/restorable elasticity which branches from a part of the main body with its internal space communicating with the main body, which appliance has been transferred in a collapsed state in a main blood vessel to a branched part branching a branch blood vessel from the main blood vessel, the device being utilized in inserting the branch portion of the appliance into the branch blood vessel, said device comprising:

an operating rod insertable into the main body from a trailing open end thereof and operable for rotation by hand, a guiding rod continuously connected to the operating rod so as to be capable of turning around with rotation of the operating rod and having a leading end extendable to an open end of the branch portion, and mooring means for releasably mooring the branch portion by a portion adjacent the open end thereof to the guiding rod, wherein the device is usable such that when the main body is moved forward with the guiding rod made to assume a predetermined position by turning, the branch portion accompanying the guiding rod is capable of advancing into the branch blood vessel together with the guiding rod, and wherein the operating rod and the guiding rod are formed by bending a flexible wire rod into a curve having a trailing side forming the operating rod and a leading side forming the guiding rod.

15. The device as set forth in claim 14, wherein the guiding rod comprises a tube having a guiding wire accommodating bore, and a guiding wire retractably accommodated in the guiding wire accommodating bore of the tube with its leading end protruding from a leading end of the tube.

16. The device as set forth in claim 15, wherein: the mooring means comprises a mooring wire forming an openable closed circuit in cooperation with the tube, the mooring wire being capable of mooring the branch portion when the closed circuit is formed by inserting the mooring wire into a portion of the branch portion and being capable of releasing from a mooring state when the closed circuit is opened by drawing the mooring wire out of the branch portion; and at least a portion of the mooring wire extending from a location of the tube adjacent a mooring position and toward a trailing side of the tube is positioned outside of the guiding wire accommodating bore.

17. The device as set forth in claim 16, wherein the tube has a portion provided with a window exposing the guiding wire accommodating bore and a mooring wire passing portion formed on an outer periphery of the tube at a location away from the window toward the trailing side of the tube, the mooring wire being passed through the mooring wire passing portion and drawn into the guiding wire accommodating bore through the window to form the closed circuit in cooperation with the tube.

18. The device as set forth in claim 16, wherein the tube is provided with two longitudinally-spaced mooring wire passing portions attached to the outer periphery thereof through which the mooring wire is passed to form the closed circuit in cooperation with the tube.

19. The device as set forth in claim 16, wherein the tube is provided with two longitudinally-spaced windows exposing the guiding wire accommodating bore, the mooring wire being drawn into the guiding wire accommodating bore through the window situated toward a trailing side of the tube and exposed through the window situated toward a leading side of the tube to form the closed circuit defined by the window situated toward the leading side and the tube.

20. The device as set forth in claim 16, wherein the tube is provided with three longitudinally-spaced windows exposing the guiding wire accommodating bore, the mooring wire being drawn into the guiding wire accommodating bore through the window situated toward a trailing side of the tube, then drawn out of the tube through the intermediate window, and again drawn into the guiding wire accommodating bore through the window situated toward a leading side of the tube, to form the closed circuit defined by the drawn-out portion of the mooring wire and the tube.

21. The device as set forth in claim 16, wherein: the tube comprises a pair of tube elements integrally related to each other and having respective wire accommodating bores, one bore serving as a guiding wire accommodating bore accommodating the guiding wire, the other bore serving as a mooring wire accommodating bore accommodating the mooring wire; and the tube element having the mooring wire accommodating bore is provided with a window exposing the mooring wire accommodating bore to form the closed circuit defined by the window and the corresponding tube element.

22. The device as set forth in claim 16, wherein the tube defines therein two wire accommodating bores separated from each other with an intermediate partition wall, one serving as a guiding wire accommodating bore accommodating the guiding wire, the other serving as a mooring wire accommodating bore accommodating the mooring wire, and is provided with a window exposing the mooring wire accommodating bore to form the closed circuit defined by the window and the tube.

23. The device as set forth in claim 14, wherein the mooring means serves also as collapsing means for maintaining the branch portion of the appliance in the collapsed state, the mooring means being capable of allowing restoration of the branch portion and releasing the branch portion from its moored state simultaneously.

24. A device for guiding an appliance comprising a guiding rod, and mooring means for releasably mooring the appliance to the guiding rod, the guiding rod comprising a tube and a guiding wire retractably accommodated in the tube with its leading end protruding from a leading end of the tube, the mooring means comprising a mooring wire forming an openable closed circuit in cooperation with the tube, the mooring wire being capable of mooring the appliance when the closed circuit is formed by inserting the mooring wire into a portion of the appliance and being capable of releasing from a mooring state when the closed circuit is opened by drawing the mooring wire out of the appliance, wherein at least a portion of the mooring wire extending from a location on the tube adjacent the mooring position toward a trailing side of the tube is positioned outside of a guiding wire accommodating bore, and wherein the tube has a portion provided with a window exposing the guiding wire accommodating bore and a mooring wire passing portion formed on an outer periphery of the tube at a location away from the window toward a trailing side of the tube, the mooring wire being passed through the mooring wire passing portion and drawn into the guiding wire accommodating bore through the window to form the closed circuit in cooperation with the tube.

25. A device for guiding an appliance comprising a guiding rod, and mooring means for releasably mooring the appliance to the guiding rod, the guiding rod comprising a tube and a guiding wire retractably accommodated in the tube with its leading end protruding from a leading end of the tube, the mooring means comprising a mooring wire forming an openable closed circuit in cooperation with the tube, wherein at least a portion of the mooring wire that extends from the closed circuit toward the trailing side is drawn out of the tube, the mooring wire being capable of mooring the appliance when the closed circuit is formed by inserting the mooring wire into a portion of the appliance and being capable of releasing from a mooring state when the closed circuit is opened by drawing the mooring wire out of the appliance, wherein at least a portion of the mooring wire extending from a location on the tube adjacent the mooring position toward a trailing side of the tube is positioned outside of a guiding wire accommodating bore, wherein the tube is provided with two longitudinally-spaced mooring wire passing portions attached to the outer periphery thereof through which the mooring wire is passed to form the closed circuit in cooperation with the tube.

26. A device for guiding an appliance comprising a guiding rod, and mooring means for releasably mooring the appliance to the guiding rod, the guiding rod comprising a tube and a guiding wire retractably accommodated in the tube with its leading end protruding from a leading end of the tube, the mooring means comprising a mooring wire forming an openable closed circuit in cooperation with the tube, the mooring wire being capable of mooring the appliance when the closed circuit is formed by inserting the mooring wire into a portion of the appliance and being capable of releasing from a mooring state when the closed circuit is opened by drawing the mooring wire out of the appliance, wherein at least a portion of the mooring wire extending from a location on the tube adjacent the mooring position toward a trailing side of the tube is positioned outside of a guiding wire accommodating bore, and wherein the tube is provided with two longitudinally-spaced windows exposing the guiding wire accommodating bore, the mooring wire being drawn into the guiding wire accommodating bore through a first one of said windows situated toward a trailing side of the tube and exposed through a second one of said windows situated toward a leading side of the tube to form the closed circuit defined by said second one of said windows situated on the leading side and the tube.

27. A device for guiding an appliance comprising a guiding rod, and mooring means for releasably mooring the appliance to the guiding rod, the guiding rod comprising a tube and a guiding wire retractably accommodated in the tube with its leading end protruding from a leading end of the tube, the mooring means comprising a mooring wire forming an openable closed circuit in cooperation with the tube, the mooring wire being capable of mooring the appliance when the closed circuit is formed by inserting the mooring wire into a portion of the appliance and being capable of releasing from a mooring state when the closed circuit is opened by drawing the mooring wire out of the appliance, wherein at least a portion of the mooring wire extending from a location on the tube adjacent the mooring position toward a trailing side of the tube is positioned outside of a guiding wire accommodating bore, and wherein the tube is provided with three longitudinally-spaced windows exposing the guiding wire accommodating bore, the mooring wire being drawn into the guiding wire accommodating bore through a first one of said windows situated toward a trailing side of the tube, then drawn out of the tube through a second intermediate one of said windows, and again drawn into the guiding wire accommodating bore through a third one of said windows situated toward a leading side of the tube, to form the closed circuit defined by the drawn-out portion of the mooring wire and the tube.

28. A device for guiding an appliance comprising a guiding rod, and mooring means for releasably mooring the appliance to the guiding rod, the guiding rod comprising a tube and a guiding wire retractably accommodated in the tube with its leading end protruding from a leading end of the tube, the mooring means comprising a mooring wire forming an openable closed circuit in cooperation with the tube, the mooring wire being capable of mooring the appliance when the closed circuit is formed by inserting the mooring wire into a portion of the appliance and being capable of releasing from a mooring state when the closed circuit is opened by drawing the mooring wire out of the appliance, wherein at least a portion of the mooring wire extending from a location on the tube adjacent the mooring position toward a trailing side of the tube is positioned outside of a guiding wire accommodating bore, and wherein the tube comprises a pair of tube elements integrally related to each other and having respective wire accommodating bores, one bore serving as a guiding wire accommodating bore accommodating the guiding wire, the other bore serving as a mooring wire accommodating bore accommodating the mooring wire; and the tube element having the mooring wire accommodating bore is provided with a window exposing the mooring wire accommodating bore to form the closed circuit defined by the window and the corresponding tube element.

* * * * *